United States Patent [19]
Melief et al.

[11] Patent Number: 5,554,724
[45] Date of Patent: Sep. 10, 1996

[54] ISOLATED TUMOR REJECTION ANTIGEN PRECURSOR MAGE-2 DERIVED PEPTIDES, AND USES THEREOF

[75] Inventors: Cornelis J. M. Melief; M. J. W. Visseren; W. M. Kast, all of Leiden, Netherlands; Pierre van der Bruggen; Thierry Boon-Falleur, both of Brussels, Belgium

[73] Assignee: University of Leiden, Leiden, Netherlands

[21] Appl. No.: 217,188

[22] Filed: Mar. 24, 1994

[51] Int. Cl.$^6$ .............................. C07K 7/00; A61K 38/08
[52] U.S. Cl. .................. 530/328; 530/300; 530/327; 530/828; 424/185.1; 424/277.1
[58] Field of Search ................... 530/328, 350, 530/300, 395, 868; 424/185.1, 277.1

[56] References Cited

U.S. PATENT DOCUMENTS

| | | | |
|---|---|---|---|
| 5,342,774 | 8/1994 | Boon et al. | 435/240.2 |
| 5,405,940 | 4/1995 | Boon et al. | 530/328 |
| 5,462,871 | 10/1995 | Boon-Falleur et al. | 435/240.2 |
| 5,487,974 | 1/1996 | Boon-Falleur et al. | 435/6 |

FOREIGN PATENT DOCUMENTS

| | | | |
|---|---|---|---|
| WO9403205 | 2/1994 | WIPO | A61K 39/00 |

OTHER PUBLICATIONS

Ding, M. et al., Biochem. Biophys. Res. Comm. 202(1):549–555, "Cloning and analysis of MAGE-1-related genes".

Townsend et al., "The Epitopes of Influenza Nucleoprotein Recognized by Cytotoxic T Lymphocytes Can Be Defined With Short Synthetic Peptides", Cell 44: 959–968 (Mar. 28, 1986).

Bjorkman et al., "The foreign antigen binding site and T cell recognition regions of class I histocompatibility antigens", Nature 329: 512–518 (Oct. 8, 1987).

Van der Bruggen et al., "A Gene Encoding an Antigenic Recognized by Cytolytic T Lymphocytes on a Human Melanoma", Science 254: 1643–1647 (1991).

Traversari et al., "A Nonapeptide Encoded by Human Gene MAGE-1 Is Recognized on HLA-A1 by Cytolytic T Lymphocytes Directed Against Tumor Antigen MZ2-E", J. Exp. Med 176: 1453–1457 (Nov. 1992).

Celis et al., "Induction of anti-tumor cytotoxic T lymphocytes in normal humans using primary cultures and synthetic peptide epitopes", Proc. Natl. Acad. Sci. USA 91: 2105–2109 (Mar. 1994).

Coulie et al., "A New Gene Coding For a Differentiation Antigen Recognized by Autologous Cytolytic T Lymphocytes on HLA-A2 Melanomas", J. Exp. Med. 180: 35–42 (Jul., 1994) (Not Prior Art).

Engelhard et al., "Structure of Peptides Associated with Class I and Class II MHC Molecules", Ann. Rev. Immunol. 12: 181–207 (1994).

Ruppert et al., "Prominent Role of Secondary Anchnor Residues in Peptide Binding to HLA-A2.1 Molecules", Cell 74: 929–937 (Sep. 10, 1993).

DeSmet et al., "Sequence and expression pattern of the human MAGE-2 gene", Immunogenetics 39: 121–129 (1994).

*Primary Examiner*—Thomas M. Cunningham
*Attorney, Agent, or Firm*—Felfe & Lynch

[57] ABSTRACT

The invention describes peptides derived from tumor rejection antigen precursor MAGE-2. These peptides bind with HLA-A2 molecules, thus presenting complexes which provoke cytolytic T cell production. The resulting "CTLs" are specific for complexes of HLA-A2 and the peptide. The complexes can be used to generate monoclonal antibodies. The cytolytic T cells produced may be used in the context of immunotherapy, such as adoptive transfer.

4 Claims, 1 Drawing Sheet

SEQUENCE LISTING ( 1 ) GENERAL INFORMATION:

( i i i ) NUMBER OF SEQUENCES: 62

( 2 ) INFORMATION FOR SEQ ID NO: 1:

( i ) SEQUENCE CHARACTERISTICS:
        ( A ) LENGTH: 11 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 1:

Ser Thr Leu Val Glu Val Thr Leu Gly Glu Val
1               5                   1 0

( 2 ) INFORMATION FOR SEQ ID NO: 2:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 2:

Leu Val Glu Val Thr Leu Gly Glu Val
1               5

( 2 ) INFORMATION FOR SEQ ID NO: 3:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein (x i) SEQUENCE DESCRIPTION: SEQ ID NO: 3:

Lys Met Val Glu Leu Val His Phe Leu
 1               5

(2) INFORMATION FOR SEQ ID NO: 4:

(i) SEQUENCE CHARACTERISTICS:
        (A) LENGTH: 10 amino acid residues
        (B) TYPE: amino acid
        (D) TOPOLOGY: linear (i i) MOLECULE TYPE: protein (x i) SEQUENCE DESCRIPTION: SEQ ID NO: 4:

Val Ile Phe Ser Lys Ala Ser Glu Tyr Leu
 1               5                   1 0

(2) INFORMATION FOR SEQ ID NO: 5:

(i) SEQUENCE CHARACTERISTICS:
        (A) LENGTH: 10 amino acid residues
        (B) TYPE: amino acid
        (D) TOPOLOGY: linear (i i) MOLECULE TYPE: protein (x i) SEQUENCE DESCRIPTION: SEQ ID NO: 5:

Tyr Leu Gln Leu Val Phe Gly Ile Glu Val
 1               5                   1 0

(2) INFORMATION FOR SEQ ID NO: 6:

(i) SEQUENCE CHARACTERISTICS:
        (A) LENGTH: 9 amino acid residues
        (B) TYPE: amino acid
        (D) TOPOLOGY: linear (i i) MOLECULE TYPE: protein (x i) SEQUENCE DESCRIPTION: SEQ ID NO: 6:

Gln Leu Val Phe Gly Ile Glu Val Val
 1               5

(2) INFORMATION FOR SEQ ID NO: 7:

(i) SEQUENCE CHARACTERISTICS:
        (A) LENGTH: 11 amino acid residues
        (B) TYPE: amino acid
        (D) TOPOLOGY: linear (i i) MOLECULE TYPE: protein (x i) SEQUENCE DESCRIPTION: SEQ ID NO: 7:

Gln Leu Val Phe Gly Ile Glu Val Val Glu Val
 1               5                   1 0

(2) INFORMATION FOR SEQ ID NO: 8:

(i) SEQUENCE CHARACTERISTICS:
        (A) LENGTH: 9 amino acid residues
        (B) TYPE: amino acid
        (D) TOPOLOGY: linear (i i) MOLECULE TYPE: protein (x i) SEQUENCE DESCRIPTION: SEQ ID NO: 8:

Ile Ile Val Leu Ala Ile Ile Ala Ile
 1               5

( 2 ) INFORMATION FOR SEQ ID NO: 9:

( i ) SEQUENCE CHARACTERISTICS:
        ( A ) LENGTH: 11 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 9:

Lys Ile Trp Glu Glu Leu Ser Met Leu Glu Val
1               5                   10

( 2 ) INFORMATION FOR SEQ ID NO: 10:

( i ) SEQUENCE CHARACTERISTICS:
        ( A ) LENGTH: 10 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 10:

Ala Leu Ile Glu Thr Ser Tyr Val Lys Val
1               5                   10

( 2 ) INFORMATION FOR SEQ ID NO: 11:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 11:

Leu Ile Glu Thr Ser Tyr Val Lys Val
1               5

( 2 ) INFORMATION FOR SEQ ID NO: 12:

( i ) SEQUENCE CHARACTERISTICS:
        ( A ) LENGTH: 11 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 12:

Gly Leu Glu Ala Arg Gly Glu Ala Leu Gly Leu
1               5                   10

( 2 ) INFORMATION FOR SEQ ID NO: 13:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 13:

Gly Leu Glu Ala Arg Gly Glu Ala Leu
1               5

( 2 ) INFORMATION FOR SEQ ID NO: 14:

( i ) SEQUENCE CHARACTERISTICS:
        ( A ) LENGTH: 9 amino acid residues ( B ) TYPE: amino acid
        ( D ) TOPOLOGY: linear ( i i ) MOLECULE TYPE: protein ( x i ) SEQUENCE DESCRIPTION: SEQ ID NO: 14:

Ala Leu Gly Leu Val Gly Ala Gln Ala
1               5

( 2 ) INFORMATION FOR SEQ ID NO: 15:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 15:

Gly Leu Val Gly Ala Gln Ala Pro Ala
1               5

( 2 ) INFORMATION FOR SEQ ID NO: 16:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 16:

Asp Leu Glu Ser Glu Phe Gln Ala Ala
1               5

( 2 ) INFORMATION FOR SEQ ID NO: 17:

( i ) SEQUENCE CHARACTERISTICS:
        ( A ) LENGTH: 10 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 17:

Asp Leu Glu Ser Glu Phe Gln Ala Ala Ile
1               5                   10

( 2 ) INFORMATION FOR SEQ ID NO: 18:

( i ) SEQUENCE CHARACTERISTICS:
        ( A ) LENGTH: 10 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 18:

Ala Ile Ser Arg Lys Met Val Glu Leu Val
1               5                   10

( 2 ) INFORMATION FOR SEQ ID NO: 19:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein (xi) SEQUENCE DESCRIPTION: SEQ ID NO: 19:

Ala Ile Ser Arg Lys Met Val Glu Leu
1               5

(2) INFORMATION FOR SEQ ID NO: 20:

(i) SEQUENCE CHARACTERISTICS:
        (A) LENGTH: 10 amino acid residues
        (B) TYPE: amino acid
        (D) TOPOLOGY: linear (ii) MOLECULE TYPE: protein (xi) SEQUENCE DESCRIPTION: SEQ ID NO: 20:

Lys Met Val Glu Leu Val His Phe Leu Leu
1               5                   10

(2) INFORMATION FOR SEQ ID NO: 21:

(i) SEQUENCE CHARACTERISTICS:
        (A) LENGTH: 11 amino acid residues
        (B) TYPE: amino acid
        (D) TOPOLOGY: linear (ii) MOLECULE TYPE: protein (xi) SEQUENCE DESCRIPTION: SEQ ID NO: 21:

Lys Met Val Glu Leu Val His Phe Leu Leu Leu
1               5                   10

(2) INFORMATION FOR SEQ ID NO: 22:

(i) SEQUENCE CHARACTERISTICS:
        (A) LENGTH: 11 amino acid residues
        (B) TYPE: amino acid
        (D) TOPOLOGY: linear (ii) MOLECULE TYPE: protein (xi) SEQUENCE DESCRIPTION: SEQ ID NO: 22:

Leu Leu Leu Lys Tyr Arg Ala Arg Glu Pro Val
1               5                   10

(2) INFORMATION FOR SEQ ID NO: 23:

(i) SEQUENCE CHARACTERISTICS:
        (A) LENGTH: 10 amino acid residues
        (B) TYPE: amino acid
        (D) TOPOLOGY: linear (ii) MOLECULE TYPE: protein (xi) SEQUENCE DESCRIPTION: SEQ ID NO: 23:

Leu Leu Lys Tyr Arg Ala Arg Glu Pro Val
1               5                   10

(2) INFORMATION FOR SEQ ID NO: 24:

(i) SEQUENCE CHARACTERISTICS:
        (A) LENGTH: 11 amino acid residues
        (B) TYPE: amino acid
        (D) TOPOLOGY: linear (ii) MOLECULE TYPE: protein (xi) SEQUENCE DESCRIPTION: SEQ ID NO: 24:

Val Leu Arg Asn Cys Gln Asp Phe Phe Pro Val
1               5                   10

( 2 ) INFORMATION FOR SEQ ID NO: 25:

( i ) SEQUENCE CHARACTERISTICS:
        ( A ) LENGTH: 11 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 25:

Tyr Leu Gln Leu Val Phe Gly Ile Glu Val Val
1               5                   10

( 2 ) INFORMATION FOR SEQ ID NO: 26:

( i ) SEQUENCE CHARACTERISTICS:
        ( A ) LENGTH: 10 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 26:

Gly Ile Glu Val Val Glu Val Val Pro Ile
1               5                   10

( 2 ) INFORMATION FOR SEQ ID NO: 27:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 27:

Pro Ile Ser His Leu Tyr Ile Leu Val
1               5

( 2 ) INFORMATION FOR SEQ ID NO: 28:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 28:

His Leu Tyr Ile Leu Val Thr Cys Leu
1               5

( 2 ) INFORMATION FOR SEQ ID NO: 29:

( i ) SEQUENCE CHARACTERISTICS:
        ( A ) LENGTH: 11 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 29:

His Leu Tyr Ile Leu Val Thr Cys Leu Gly Leu
1               5                   10

( 2 ) INFORMATION FOR SEQ ID NO: 30:

( i ) SEQUENCE CHARACTERISTICS:
        ( A ) LENGTH: 9 amino acid residues (B) TYPE: amino acid
(D) TOPOLOGY: linear (ii) MOLECULE TYPE: protein (xi) SEQUENCE DESCRIPTION: SEQ ID NO: 30:

```
Tyr  Ile  Leu  Val  Thr  Cys  Leu  Gly  Leu
1                      5
```

(2) INFORMATION FOR SEQ ID NO: 31:

(i) SEQUENCE CHARACTERISTICS:
(A) LENGTH: 9 amino acid residues
(B) TYPE: amino acid
(D) TOPOLOGY: linear (ii) MOLECULE TYPE: protein (xi) SEQUENCE DESCRIPTION: SEQ ID NO: 31:

```
Cys  Leu  Gly  Leu  Ser  Tyr  Asp  Gly  Leu
1                      5
```

(2) INFORMATION FOR SEQ ID NO: 32:

(i) SEQUENCE CHARACTERISTICS:
(A) LENGTH: 10 amino acid residues
(B) TYPE: amino acid
(D) TOPOLOGY: linear (ii) MOLECULE TYPE: protein (xi) SEQUENCE DESCRIPTION: SEQ ID NO: 32:

```
Cys  Leu  Gly  Leu  Ser  Tyr  Asp  Gly  Leu  Leu
1                      5                     10
```

(2) INFORMATION FOR SEQ ID NO: 33:

(i) SEQUENCE CHARACTERISTICS:
(A) LENGTH: 9 amino acid residues
(B) TYPE: amino acid
(D) TOPOLOGY: linear (ii) MOLECULE TYPE: protein (xi) SEQUENCE DESCRIPTION: SEQ ID NO: 33:

```
Val  Met  Pro  Lys  Thr  Gly  Leu  Leu  Ile
1                      5
```

(2) INFORMATION FOR SEQ ID NO: 34:

(i) SEQUENCE CHARACTERISTICS:
(A) LENGTH: 10 amino acid residues
(B) TYPE: amino acid
(D) TOPOLOGY: linear (ii) MOLECULE TYPE: protein (xi) SEQUENCE DESCRIPTION: SEQ ID NO: 34:

```
Val  Met  Pro  Lys  Thr  Gly  Leu  Leu  Ile  Ile
1                      5                     10
```

(2) INFORMATION FOR SEQ ID NO: 35:

(i) SEQUENCE CHARACTERISTICS:
(A) LENGTH: 11 amino acid residues
(B) TYPE: amino acid
(D) TOPOLOGY: linear (ii) MOLECULE TYPE: protein ( x i ) SEQUENCE DESCRIPTION: SEQ ID NO: 35:

Val Met Pro Lys Thr Gly Leu Leu Ile Ile Val
1               5                   10

( 2 ) INFORMATION FOR SEQ ID NO: 36:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 36:

Gly Leu Leu Ile Ile Val Leu Ala Ile
1               5

( 2 ) INFORMATION FOR SEQ ID NO: 37:

( i ) SEQUENCE CHARACTERISTICS:
        ( A ) LENGTH: 10 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 37:

Gly Leu Leu Ile Ile Val Leu Ala Ile Ile
1               5                   10

( 2 ) INFORMATION FOR SEQ ID NO: 38:

( i ) SEQUENCE CHARACTERISTICS:
        ( A ) LENGTH: 11 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 38:

Gly Leu Leu Ile Ile Val Leu Ala Ile Ile Ala
1               5                   10

( 2 ) INFORMATION FOR SEQ ID NO: 39:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 39:

Leu Leu Ile Ile Val Leu Ala Ile Ile
1               5

( 2 ) INFORMATION FOR SEQ ID NO: 40:

( i ) SEQUENCE CHARACTERISTICS:
        ( A ) LENGTH: 10 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 40:

Leu Leu Ile Ile Val Leu Ala Ile Ile Ala
1               5                   10

( 2 ) INFORMATION FOR SEQ ID NO: 41:

( i ) SEQUENCE CHARACTERISTICS:
        ( A ) LENGTH: 11 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 41:

```
Leu Leu Ile Ile Val Leu Ala Ile Ile Ala Ile
1               5                   10
```

( 2 ) INFORMATION FOR SEQ ID NO: 42:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 42:

```
Leu Ile Ile Val Leu Ala Ile Ile Ala
1               5
```

( 2 ) INFORMATION FOR SEQ ID NO: 43:

( i ) SEQUENCE CHARACTERISTICS:
        ( A ) LENGTH: 10 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 43:

```
Leu Ile Ile Val Leu Ala Ile Ile Ala Ile
1               5                   10
```

( 2 ) INFORMATION FOR SEQ ID NO: 44:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 44:

```
Ile Ile Ala Ile Glu Gly Asp Cys Ala
1               5
```

( 2 ) INFORMATION FOR SEQ ID NO: 45:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 45:

```
Lys Ile Trp Glu Glu Leu Ser Met Leu
1               5
```

( 2 ) INFORMATION FOR SEQ ID NO: 46:

( i ) SEQUENCE CHARACTERISTICS:
        ( A ) LENGTH: 11 amino acid residues ( B ) TYPE: amino acid
         ( D ) TOPOLOGY: linear ( i i ) MOLECULE TYPE: protein ( x i ) SEQUENCE DESCRIPTION: SEQ ID NO: 46:

Leu Met Gln Asp Leu Val Gln Glu Asn Tyr Leu
 1               5                   1 0

( 2 ) INFORMATION FOR SEQ ID NO: 47:

( i ) SEQUENCE CHARACTERISTICS:
         ( A ) LENGTH: 9 amino acid residues
         ( B ) TYPE: amino acid
         ( D ) TOPOLOGY: linear ( i i ) MOLECULE TYPE: protein ( x i ) SEQUENCE DESCRIPTION: SEQ ID NO: 47:

Phe Leu Trp Gly Pro Arg Ala Leu Ile
 1               5

( 2 ) INFORMATION FOR SEQ ID NO: 48:

( i ) SEQUENCE CHARACTERISTICS:
         ( A ) LENGTH: 9 amino acid residues
         ( B ) TYPE: amino acid
         ( D ) TOPOLOGY: linear ( i i ) MOLECULE TYPE: protein ( x i ) SEQUENCE DESCRIPTION: SEQ ID NO: 48:

Leu Ile Glu Thr Ser Tyr Val Lys Val
 1               5

( 2 ) INFORMATION FOR SEQ ID NO: 49:

( i ) SEQUENCE CHARACTERISTICS:
         ( A ) LENGTH: 11 amino acid residues
         ( B ) TYPE: amino acid
         ( D ) TOPOLOGY: linear ( i i ) MOLECULE TYPE: protein ( x i ) SEQUENCE DESCRIPTION: SEQ ID NO: 49:

Ala Leu Ile Glu Thr Ser Tyr Val Lys Val Leu
 1               5                   1 0

( 2 ) INFORMATION FOR SEQ ID NO: 50:

( i ) SEQUENCE CHARACTERISTICS:
         ( A ) LENGTH: 10 amino acid residues
         ( B ) TYPE: amino acid
         ( D ) TOPOLOGY: linear ( i i ) MOLECULE TYPE: protein ( x i ) SEQUENCE DESCRIPTION: SEQ ID NO: 50:

Thr Leu Lys Ile Gly Gly Glu Pro His Ile
 1               5                   1 0

( 2 ) INFORMATION FOR SEQ ID NO: 51:

( i ) SEQUENCE CHARACTERISTICS:
         ( A ) LENGTH: 11 amino acid residues
         ( B ) TYPE: amino acid
         ( D ) TOPOLOGY: linear ( i i ) MOLECULE TYPE: protein ( x i ) SEQUENCE DESCRIPTION: SEQ ID NO: 51:

His Ile Ser Tyr Pro Pro Leu His Glu Arg Ala
1               5                   10

( 2 ) INFORMATION FOR SEQ ID NO: 52:

( i ) SEQUENCE CHARACTERISTICS:
  ( A ) LENGTH: 9 amino acid residues
  ( B ) TYPE: amino acid
  ( D ) TOPOLOGY: linear ( i i ) MOLECULE TYPE: protein ( x i ) SEQUENCE DESCRIPTION: SEQ ID NO: 52:

Gln Thr Ala Ser Ser Ser Ser Thr Leu
1               5

( 2 ) INFORMATION FOR SEQ ID NO: 53:

( i ) SEQUENCE CHARACTERISTICS:
  ( A ) LENGTH: 10 amino acid residues
  ( B ) TYPE: amino acid
  ( D ) TOPOLOGY: linear ( i i ) MOLECULE TYPE: protein ( x i ) SEQUENCE DESCRIPTION: SEQ ID NO: 53:

Gln Thr Ala Ser Ser Ser Ser Thr Leu Val
1               5                   10

( 2 ) INFORMATION FOR SEQ ID NO: 54:

( i ) SEQUENCE CHARACTERISTICS:
  ( A ) LENGTH: 9 amino acid residues
  ( B ) TYPE: amino acid
  ( D ) TOPOLOGY: linear ( i i ) MOLECULE TYPE: protein ( x i ) SEQUENCE DESCRIPTION: SEQ ID NO: 54:

Val Thr Leu Gly Glu Val Pro Ala Ala
1               5

( 2 ) INFORMATION FOR SEQ ID NO: 55:

( i ) SEQUENCE CHARACTERISTICS:
  ( A ) LENGTH: 10 amino acid residues
  ( B ) TYPE: amino acid
  ( D ) TOPOLOGY: linear ( i i ) MOLECULE TYPE: protein ( x i ) SEQUENCE DESCRIPTION: SEQ ID NO: 55:

Val Thr Lys Ala Glu Met Leu Glu Ser Val
1               5                   10

( 2 ) INFORMATION FOR SEQ ID NO: 56:

( i ) SEQUENCE CHARACTERISTICS:
  ( A ) LENGTH: 11 amino acid residues
  ( B ) TYPE: amino acid
  ( D ) TOPOLOGY: linear ( i i ) MOLECULE TYPE: protein ( x i ) SEQUENCE DESCRIPTION: SEQ ID NO: 56:

Val Thr Lys Ala Glu Met Leu Glu Ser Val Leu
1               5                   10

( 2 ) INFORMATION FOR SEQ ID NO: 57:

( i ) SEQUENCE CHARACTERISTICS:
        ( A ) LENGTH: 11 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 57:

Val Thr Cys Leu Gly Leu Ser Tyr Asp Gly Leu
1               5                   10

( 2 ) INFORMATION FOR SEQ ID NO: 58:

( i ) SEQUENCE CHARACTERISTICS:
        ( A ) LENGTH: 9 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 58:

Lys Thr Gly Leu Leu Ile Ile Val Leu
1               5

( 2 ) INFORMATION FOR SEQ ID NO: 59:

( i ) SEQUENCE CHARACTERISTICS:
        ( A ) LENGTH: 10 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 59:

Lys Thr Gly Leu Leu Ile Ile Val Leu Ala
1               5                   10

( 2 ) INFORMATION FOR SEQ ID NO: 60:

( i ) SEQUENCE CHARACTERISTICS:
        ( A ) LENGTH: 11 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 60:

Lys Thr Gly Leu Leu Ile Ile Val Leu Ala Ile
1               5                   10

( 2 ) INFORMATION FOR SEQ ID NO: 61:

( i ) SEQUENCE CHARACTERISTICS:
        ( A ) LENGTH: 11 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 61:

His Thr Leu Lys Ile Gly Gly Glu Pro His Ile
1               5                   10

( 2 ) INFORMATION FOR SEQ ID NO: 62:

( i ) SEQUENCE CHARACTERISTICS:
        ( A ) LENGTH: 9 amino acid residues (B) TYPE: amino acid
(D) TOPOLOGY: linear (ii) MOLECULE TYPE: protein (xi) SEQUENCE DESCRIPTION: SEQ ID NO: 62:

Met Leu Asp Leu Gln Pro Glu Thr Thr
1               5

ISOLATED TUMOR REJECTION ANTIGEN PRECURSOR MAGE-2 DERIVED PEPTIDES, AND USES THEREOF

FIELD OF THE INVENTION

This invention relates to immunogenetics and to peptide chemistry. More particularly, it relates to peptides, especially undercapeptides, decapeptides, and nonapeptides useful in various ways, including immunogens and as ligands for the HLA-A2 molecule. More particularly, it relates to a so-called "tumor rejection antigen", derived from the tumor rejection antigen precursor encoded by gene MAGE-2, and presented by the MHC-class I molecule HLA-A2.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum⁻ variants fail to form progressive tumors because they initiate an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48: 2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and the class of antigens referred to as "tum–" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9:1041–1050 (1990), and Sibille et al., J. Exp. Med. 172:35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra), and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum⁺, such as the line referred to as "P1", and can be provoked to produce tum⁻ variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

PCT application PCT/US92/04354, filed on May 22, 1992 assigned to the same assignee as the subject application, teaches a family of human tumor rejection antigen precursor coding genes, referred to as the MAGE family. Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. See also Traversari et al., Immunogenetics 35: 145 (1992); van der Bruggen et al., Science 254: 1643 (1991). The mechanism by which a protein is processed and presented on a cell surface has now been fairly well documented. A cursory review of the development of the field may be found in Barinaga, "Getting 'Some Backbone': How MHC Binds Peptides", Science 257: 880 (1992); also, see Fremont et al., Science 257: 919 (1992); Matsumura et al., Science 257: 927 (1992); Latron et al., Science 257: 964 (1992). These papers generally point to a requirement that the peptide which binds to an MHC/HLA molecule be nine amino acids long (a "nonapeptide"), and to the importance of the first and ninth residues of the nonapeptide.

Studies on the MAGE family of genes have now revealed that a particular nonapeptide is in fact presented on the surface of some tumor cells, and that the presentation of the nonapeptide requires that the presenting molecule be HLA-A1. Complexes of the MAGE-1 tumor rejection antigen (the "TRA" or "nonapeptide") leads to lysis of the cell presenting it by cytolytic T cells ("CTLs").

Attention is drawn, e.g., to concurrently filed application Ser. No. 08/217,187 to Traversari et al., and Ser. No. 08/217,186 to Towsend et al., both of which present work on other MAGE-derived peptides.

Research presented in, e.g., U.S. patent application Ser. No. 07/938,334 filed Aug. 31, 1992, and in U.S. patent application Ser. No. 073,103, filed Jun. 7, 1993, found that when comparing homologous regions of various MAGE genes to the region of the MAGE1 gene coding for the relevant nonapeptide, there is a great deal of homology. Indeed, these observations lead to one of the aspects of the invention disclosed and claimed therein, which is a family of nonapeptides all of which have the same N-terminal and C-terminal amino acids. These nonapeptides were described as being useful for various purposes which includes their use as immunogens, either alone or coupled to carrier peptides. Nonapeptides are of sufficient size to constitute an antigenic epitope, and the antibodies generated thereto were described as being useful for identifying the nonapeptide, either as it exists alone, or as part of a larger polypeptide.

These references, especially Ser. No. 073,103, showed a connection between HLA-A1 and MAGE-3; however, only about 26% of the caucasian population and 17% of the negroid population presents HLA-A1 molecules on cell surfaces. Thus, it would be useful to have additional information on peptides presented by other types of MHC molecules, so that appropriate portions of the population may benefit from the research discussed supra.

It has now been found that antigen presentation of MAGE-2 derived peptides set forth, in the disclosure which follows, identifies peptides which complex with MHC class I molecule HLA- 2. The ramifications of this discovery, which include therapeutic and diagnostic uses, are among the subjects of the invention, set forth in the disclosure which follows.

DETAILED DESCRIPTION OF PREFERRED EMBODIMENTS

Example 1

Experimental Conditions

Figure 1:
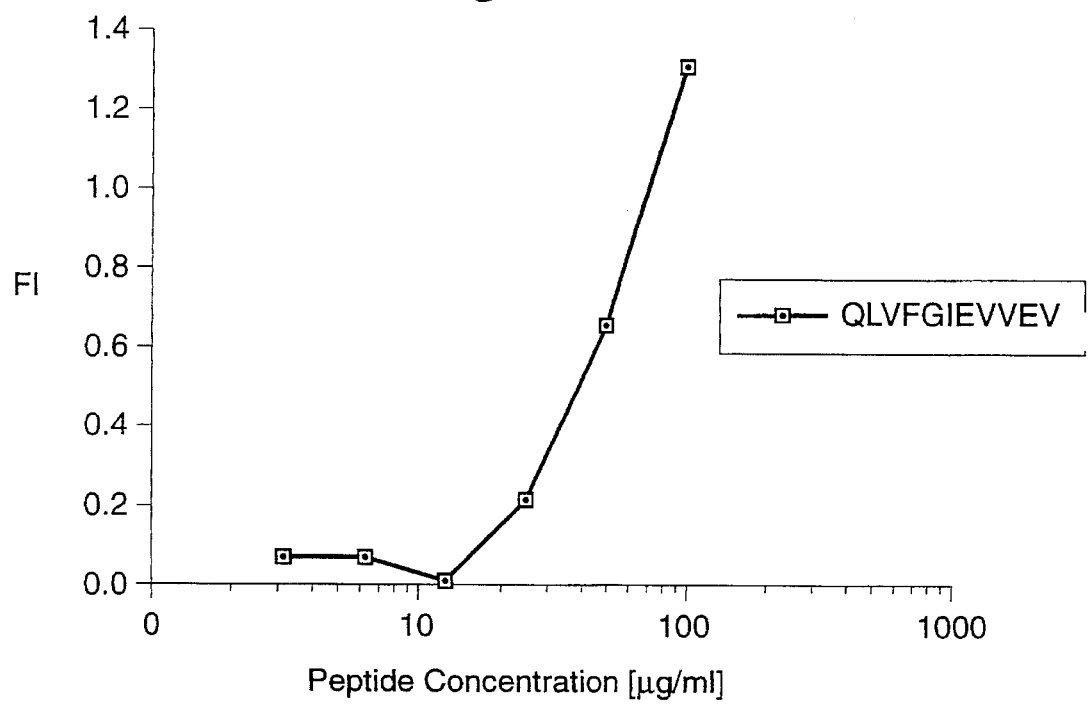
FIG. 1 is an exemplary graph showing the calculation of peptide concentration which includes 0.5 maximum upregulation of HLA-A2.1

All experiments were performed at room temperature unless stated otherwise. All Fmoc protected aminoacids, synthesis polymers, peptides and TFA were stored at –20° C.
Peptide Synthesis Peptides were synthesized by solid phase strategies on an automated multiple peptide synthesizer (Abimed AMS 422) (see Gausepohl and Frank, Biotech, September 1990; Gausepohl et al., in E Giralt and D. Andreu, (eds). Peptides 1990: 206–207 (1990).

The peptides were made in various runs, in each of which 48 different peptides were synthesized simultaneously.

Tentagel S AC (Rapp et al., In Innovation and Perspectives in Solid Phase Peptide Synthesis, 205–210 (1990)); Sheppard and Williams, Peptide Protein Res. 20: 451–454 (1982) a graft polymer of polyethyleneglycol spacer arms on a polystyrene matrix, was used as a resin (40–60 mg per peptide, 10 μmol Fmoc amino acid loading).

Repetitive couplings were performed by adding a mixture of 90 μl 10.67 M BOP (Gausepohl et al., Peptides 1988: 241–243 (1988); Castro et al., Tet. Lett 14: 1219–1222 (1975)) in NMP, 20 μl NMM in NMP 2/1 (v/v) and 100 μl of an 0.60 M solution of the appropriate Fmocamino acid (Fields and Noble, Int. J. Pep. Prot. Res. 35: 161–214 (1990)) in NMP (6-fold excess) to each reaction vessel. At 70% of the reaction time approximately 50 μl dichloromethane was added to each reaction vessel.

Fmoc-deprotection was performed by adding 3 times 0.8 ml of piperidine/DMA 1/4 (v/v) to each reaction vessel.

Coupling- and deprotection times were increased as the synthesis proceeded, starting with 30 min and 3 times 3 min respectively.

Washings after couplings and Fmoc-deprotections were done with 6 times 1.2 ml DMA. After the required sequence had been reached and the last Fmoc-protection was removed the peptidylresin was washed extensively with DMA, dichloromethane, dichloromethane/ether 1/1 (v/v) and ether respectively, and dried.

Peptide Cleavage and Isolation

Cleavage of the peptides from the resin and removal of the side chain protecting groups was performed by adding 6 times 200 μl TFA/water 19/1 (v/v) at 5 min intervals to each reaction vessel, thus yielding free carboxylic peptides. For Trp-containing peptides TFA/water/ethanethiol 18/1/1 (v/v/v) was used.

Two hours after the first TFA addition the peptides were precipitated from the combined filtrates by addition of 10 ml ether/pentane 1/1 (v/v) and cooling to −20° C. The peptides were isolated by centrifugation (−20° C., 2500 g, 10 min).

After treatment of the pellet with ether/pentane 1/1 (v/v) and isolation by the same centrifugation procedure, the peptides were dried at 45° C. for 15 min.

Each of the peptides was dissolved in 2 ml water (or 2 ml 10 vol. % acetic acid), the solution frozen in liquid nitrogen for 3 min, and lyophilized while being centrifuged (1300 rpm, 8–16 h).

Analysis and Purification

The purity of the peptides was determined by reversed phase RPLC; an aliquot of about 50 nmol was dissolved in 100 μl 30 vol. % acetic acid. Of this solution 30 μl was applied to an RP-HPLC system equipped with a ternary solvent system; A: water, B: acetonitrile, C: 2 vol. % TFA in water.

Gradient elution (1.0 ml/min) was performed from 90% A, 5% B, 5% C to 20% A, 75% B, 5%C in 30 min. Detection was at 214 nm.

Samples taken at random were analyzed by mass spectrometry on a PDMS. The 31 binding peptides were all analyzed by mass spectrometry on a PDMS and by quantative amino acid analysis after hydrolysis on a HP Aminoquant. Of all analyzed samples the difference between calculated and measured masses was within the experimental error (0.1%) as specified by the producer of the equipment used. All aminoacid compositions were as expected.

Example 2

Peptides

Of all 71MAGE-2 peptides that had been freeze dried, 1 mg was weighed and dissolved in 10 μl of DMSO. Of all dissolved peptides a dilution of 0.5 mg/ml in 0.9% NaCl was made and the pH was neutralized to pH 7 with 5% acetic acid diluted in distilled water ($CH_3COOH$, Merck Darmstadt, Germany:) or 1N NaOB diluted in distilled water (Merck Darmstadt, Germany:).

Cells

174CEM.T2 cells were cultured in Iscove's modified Dulbecco's medium (Biochrom KG Seromed Berlin, Germany:) supplemented with 100 IU/ml penicillin (Biocades Pharma, Leiderdorp, The Netherlands), 100 μg/ml kanamycin (Sigma St. Louis, USA:), 2 mM glutamine (ICN Biomedicals Inc. Costa Mesa, CA, USA:) and 10% fetal calf serum (FCS, Hyclone Laboratories Inc. Logan, Utah, USA:). Cells were cultured at a density of $2.5 \times 10^5$/ml during 3 days at 37° C., 5% $CO_2$ in humified air.

Peptide Binding

174CEM.T2 cells were washed twice in culture medium without FCS and put in serum-free culture medium to a density of $2 \times 10^6$ cells/ml. Of this suspension 40 μl was put into a V bottomed 96 well plate (Greiner GmbH, Frickenhausen, Germany:) together with 10 μl of twofold serial dilutions in 0.9% NaCl of the individual peptide dilutions (ranging from 500 μg/ml to 15.6 μg/ml ). The end concentrations range from 200 μg/ml to 3.1 μg/ml peptide with $8 \times 10^4$ 174CEM.T2 cells. This solution was gently agitated for 3 minutes after which an incubation time of 16 hours at 37° C., 5% $CO_2$ in humified air took place. Then cells were washed once with 100 μl 0.9% NaCl, 0.5% bovine serum albumin ( Sigma St. Louis, USA:), 0.02% $NaN_3$ (Merck Darmstadt, Germany:822335). After a centrifuge round of 1200 rpm the pellet was resuspended in 50 μl of saturating amounts of HLA-A2.1 specific mouse monoclonal antibody BB7.2 for 30 minutes at 4° C. Then cells were washed twice and incubated for 30 minutes with $F(ab)_2$ fragments of goat anti-mouse IgG that had been conjugated with fluorescein isothiocyanate (Tago Inc Burlingame, Calif. USA:) in a dilution of 1:40 and a total volume of 25 μl.

After the last incubation, cells were washed twice and fluorescence was measured at 488 nanometer on a FACScan flow-cytometer (Becton Dickinson, Franklin Lakes, N.J., USA). The concentration at which the 0.5 maximum upregulation of HLA-A2.1 on 174CEM.T2 cells was achieved was determined using graphs in which the fluorescence index was plotted against the peptide concentration. The results are shown in Table I.

TABLE I

Binding affinities of peptides derived from human melanoma associated protein MAGE-2 that fit the HLA-A2.1 motif compilation of Falk et al., Nature 351: 290–296 (1992); Hunt et al., Science 255: 1261–1263 (1993): Nijman et al., J. Immunotherapy 14: 121–126 (1993)).

| SEQ. ID. NO. | sequence | residues | peptide concentration that induces 0.5 maximum FI |
|---|---|---|---|
| 12 | GLEARGEALGL | 15–25 | >100 μg/ml |
| 13 | GLEARGEAL | 15–23 | 60 μg/ml4 |
| 14 | ALGLVGAQA | 22–30 | >100 μg/ml |
| 15 | GLVGAQAPA | 24–32 | 65 μg/ml |
| 16 | DLESEFQAA | 100–108 | >100 μg/ml |
| 17 | DLESEFQAAI | 100–109 | >100 μg/ml |
| 18 | AISRKMVELV | 108–117 | >100 μg/ml |
| 19 | AISRKMVEL | 108–116 | >100 μg/ml |
| 3 | KMVELVHFL | 112–120 | 40 μg/ml |
| 20 | KMVELVHFLL | 112–221 | >100 μg/ml |
| 21 | KMVELVHFLLL | 112–122 | >100 μg/ml |
| 22 | LLLKYRAREPV | 120–130 | >100 μg/ml |
| 23 | LLKYRAREPV | 121–130 | >100 μg/ml |
| 24 | VLRNCQDFFPV | 139–149 | >100 μg/ml |
| 4 | VIFSKASEYL | 149–158 | 35 μg/ml |
| 5 | YLQLVFGIEV | 157–166 | 35 μg/ml |
| 25 | YLQLVFGIEVV | 157–167 | >100 μg/ml |
| 6 | QLVFGIEVV | 159–167 | 25 μg/ml |
| 7 | QLVFGIEVVEV | 159–169 | 30 μg/ml |
| 26 | GIEVVEVVPI | 163–172 | >100 μg/ml |
| 27 | PISHLYILV | 171–279 | 55 μg/ml |
| 28 | HLYILVTCL | 174–182 | >100 μg/ml |
| 29 | HLYILVTCLGL | 174–184 | >100 μg/ml |
| 30 | YILVTCLGL | 176–184 | >100 μg/ml |
| 31 | CLGLSYDGL | 181–189 | 65 μg/ml |
| 32 | CLGLSYDGLL | 181–190 | >100 μg/ml |
| 33 | VMPKTGLLI | 195–203 | >100 μg/ml |
| 34 | VMPKTGLLII | 195–204 | >100 μg/ml |
| 35 | VMPKTGLLIIV | 195–205 | >100 μg/ml |
| 36 | GLLIIVLAI | 200–208 | >100 μg/ml |
| 37 | GLLIIVLAII | 200–209 | >100 μg/ml |
| 38 | GLLIIVLAIIA | 200–210 | >100 μg/ml |
| 39 | LLIIVLAII | 201–209 | >100 μg/ml |
| 40 | LLIIVLAIIA | 201–210 | >100 μg/ml |
| 41 | LLIIVLAIIAI | 201–211 | >100 μg/ml |
| 42 | LIIVLAIIA | 202–210 | >100 μg/ml |
| 43 | LIIVLAIIAI | 202–211 | >100 μg/ml |
| 8 | IIVLAIIAI | 203–211 | 20 μg/ml |
| 44 | IIAIEGDCA | 208–216 | >100 μg/ml |
| 45 | KIWEELSML | 220–228 | >100 μg/ml |
| 9 | KIWEELSMLEV | 220–230 | 25 μg/ml |
| 46 | LMQDLVQENYL | 246–256 | >100 μg/ml |
| 47 | FLWGPRALI | 271–279 | 65 μg/ml |
| 10 | ALIETSYVKV | 277–286 | 20 μg/ml |

TABLE I-continued

Binding affinities of peptides derived from human melanoma associated protein MAGE-2 that fit the HLA-A2.1 motif compilation of Falk et al., Nature 351: 290–296 (1992); Hunt et al., Science 255: 1261–1263 (1993): Nijman et al., J. Immunotherapy 14: 121–126 (1993)).

| SEQ. ID. NO. | sequence | residues | peptide concentration that induces 0.5 maximum FI |
|---|---|---|---|
| 49 | ALIETSYVKVL | 277–287 | >100 μg/ml |
| 11 | LIETSYVKV | 278–286 | 30 μg/ml |
| 63 | LIETSYVKVL | 278–287 | 55 μg/ml |
| 50 | TLKIGGEPHI | 290–299 | >100 μg/ml |
| 51 | HISYPPLHERA | 298–308 | >100 μg/ml |

The 174CEM. T2 cell line expresses "empty" and unstable HLA-A2.1 molecules that can be stabilized when a peptide is binding to the peptide presenting groove of these molecules. A stabilized BLA-A2.1 molecule that will not easily degrade is the result of binding of an analyzed peptide. This leads to an increase in cell surface expression of the HLA-A2.1 molecule. The fluorescence index is a measure for the amount of upregulation of HLA-A2.1 molecules. This fluorescence index is calculated according to the following formula:

MF=Mean Fluorescence $$FI = \text{Fluorescence Index} = \frac{(MF)\text{experiment} - (MF)\text{blank}}{(MF)\text{blank}}$$

Fluorescence Index of the background fluorescence is 0.

Results

In order to identify MAGE-2 peptides that could bind to HLA-A2.1 molecules expressed by 174CEM.T2 cells, the amino acid sequence of MAGE-2 was examined in accordance with van der Bruggen et al., Science 254: 1643–1647 (1991). All peptides of nine, ten or eleven amino acid that fitted the published HLA-A2.1 binding motif were examined (Table I).

Only the peptides of SEQ ID Nos: 1–11 of Table II were able to upregulate the expression of HLA-A2.1 molecules at low peptide concentration, indicating their binding to the HLA-A2.1 molecule as described in Example 2. None of the 50 other peptides were able to do this. The results of the fluorescence measurement are given in Table I and II. The 0.5 maximum upregulation of HLA-A2.1 molecules on 174CEM.T2 cells was determined using graphs in which the FI was plotted against the peptide concentration for each individual peptide. These experiments indicate that only a limited proportion of p,prides that fit the HLA-A2.1 motif have the ability to bind to this HLA molecule with high affinity and are therefore the only candidates of the MAGE-2 protein to be recognized by human CTL, because CTL recognize peptides only when bound to HLA molecules.

TABLE II

Binding affinities of additional peptides derived from human melanoma associated protein MAGE-2 that fit the extended HLA-A2.1 motif (Ruppert et al).

| SEQ. ID NO. | sequence | residues | peptide concentration that induces 0.5 maximum FI |
|---|---|---|---|
| 52 | QTASSSSTL | 37–45 | >100 μg/ml |
| 53 | QTASSSSTLV | 37–46 | >100 μg/ml |

TABLE II-continued

Binding affinities of additional peptides derived from human melanoma associated protein MAGE-2 that fit the extended HLA-A2.1 motif (Ruppert et al).

| SEQ. ID NO. | sequence | residues | peptide concentration that induces 0.5 maximum FI |
|---|---|---|---|
| 1 | STLVEVTLGEV | 43–53 | 45 μg/ml |
| 54 | VTLGEVPAA | 46–56 | >100 μg/ml |
| 55 | VTKAEMLESV | 130–139 | 70 μg/ml |
| 56 | VTKAEMLESVL | 130–140 | >100 μg/ml |
| 57 | VTCLGLSYDGL | 179–189 | >100 μg/ml |
| 58 | KTGLLIIVL | 198–206 | 65 μg/ml |
| 59 | KTGLLIIVLA | 198–207 | 80 μg/ml |
| 60 | KTGLLIIVLAI | 198–208 | >100 μg/ml |
| 61 | HTLKIGGEPHI | 289–299 | >100 μg/ml |

TABLE III

Peptides derived from melanoma protein MAGE-2 binding to HLA-A2.1

| Peptide No. | Amino acid sequence | region | SEQ ID NO |
|---|---|---|---|
| 1 | STLVEVTLGEV | residues 43–53 | 1 |
| — | LVEVTLGEV | residues 45–53 | 2 |
| 2 | KMVELVHFL | residues 112–120 | 3 |
| 3 | VIFSKASEYL | residues 149–158 | 4 |
| 4 | YLQLVFGIEV | residues 157–166 | 5 |
| 5 | QLVFGIEVV | residues 159–167 | 6 |
| 6 | QLVFGIEVVEV | residues 159–169 | 7 |
| 7 | IIVLAIIAI | residues 203–211 | 8 |
| 8 | KIWEELSMLEV | residues 220–230 | 9 |
| 9 | ALIETSYVKV | residues 277–286 | 10 |
| 10 | LIETSYVKV | residues 278–286 | 11 |

Most HLA-A2.1 binding peptides were found using the HLA-A2.1 motif, in accordance with Falk et al., Nature 351: 290–296 (1991); Hunt et al., Science 255: 1261–1263 (1992); and Nijman et al., J. Immunotherapy 14: 121–126 (1993). Only one additional HLA-A2.1 binding peptide was found using the extended HLA-A2.1 motif of Ruppert et al., Cell 74: 929–937 (1993).

Example 3

This example shows the in vitro induction of primary immune responses. As an illustration for the possibility of inducing primary responses in general, including MAGE-2 peptides, such responses against HPV peptides using the processing defective cell line 174CEM.T2 are shown.

The expression of HLA-A2.1 on 174CEM.T2 cells (T2) is increased by incubating T2 cells in medium containing relevant peptide. T2 cells will present the relevant peptide bound to HLA-A2.1 in high amount and therefore are good antigen presenting cells (APC). In the response inducing method described recently (Kast et al., J. Immunotherapy 14: 115–120 (1993) the T2 cell line is used as APC and post-Fico mononuclear cells are used as responder cells.

Method

1) Peptide Loading of HLA-A2.1 On T2

T2 cells in a concentration of $2 \times 10^6$ cells per ml were incubated for 13 h at 37° C. in a T 25 flask (Becton Dickinson, Falcon, Plymouth England) in serum-free IMDM (=Iscoves Modified Dulbecco's Medium: Biochrom KG, Seroreed Berlin, Germany,) with glutamine (2 mM, ICN Biochemicals Inc., Costa Meisa, USA,), antibiotics (100 IU/ml penicillin (Brocades Pharma, Leiderdorp, The Netherlands, 100 μg/ml kanamycin (Sigma, St. Louis, USA,) and the selected peptide from HPV MLDLQPETT (SEQ ID NO: 12) in a concentration of 80 μg/ml.

2) Mitomycin C Treatment of T2 Antigen Presenting cells (APC)

These incubated T2 cells were spun down and subsequently resuspended at in a density of 20–10$^6$ cells/ml with Mitomycin C (50 μg/ml) in serum-free RPMI (Gibco Paisley, Scotland,) medium for 1 h at 37° C. Hereafter the T2 cells were washed three times in RPMI.

3) Preparing for Primary Immune Response Induction

All wells of a 96-well-U-bottom plate (Costar, Cambridge, USA,) were filled with 100,000 Mitomycin C-treated T2 cells in 50 μl serum-free, complete RPMI medium (glutamine (2mM, ICN Biochemcals Inc., Costa Meisa, USA,), penicillin (100 IU/ml, Brocades Pharma, Leiderdorp, The Netherlands), kanamycin (100 μg/ml, Sigma, St. Louis, USA,)) and the peptide MLDLQPETT (SEQ ID NO: 12) in a concentration of 80 μg/ml.

4) Responder Cells

Responder cells are mononuclear peripheral blood lymphocytes (PBL) of a HLA-A2.1 subtyped donor (=C.B.). The PBL were separated from bully coats by Ficoll-procedure (Ficoll preparation: Lymphoprep of Nycomed-pharma, Oslo, Norway,) and washed twice in RPMI. After separation and washing, the PBL were resuspended in complete RPMI medium with 30% human pooled serum (HPS) (HPS is tested for suppression activity in mixed lymphocyte cultures).

5) Incubation of Primary Immune Response 400,000 PBL-C.B. in 50 μl of medium (the medium described in paragraph 4, supra) were added to each well of the 96- well-U-bottom plate already filled with T2 cells and cultured for 7 days at 37° C. in an incubator with 5% CO$_2$ and 90% humidity.

6) Restimulation (day 7)

On day 7 after incubation of PBLs, peptide MLDLQPETT (SEQ ID NO: 62) and T2 cells (described supra, PBLs were restimulated with peptide MLDLQPETT (SEQ ID NO: 62). For this purpose all cells and medium out of the 96 wells were harvested. Viable cells were isolated by the Ficoll-procedure and washed in RPMI. In a new 96-well-U-bottom plate 50,000 of these viable cells were seeded in each well together with 50 μl complete RPMI medium with 15% HPS. Per well 20,000 autologous, irradiated (3000 rad) PBLs and 50,000 autologous, irradiated (10000 rad) EBV-transformed B-lymphocytes (=EBV-C.B. ) were added together with 50 μl of complete RPMI medium with 15% HPS and peptide MLDLQPETT (SEQ ID NO; 62) in a concentration of 80 μg/ml. The cells were cultured for 7 days at 37° C. in an incubator with 5% CO$_2$ and 90% humidity.

7) Restimulation (day 14)

On day 14 after incubation of PBLs, peptide MLDLQPETT (SEQ ID NO: 62) and T2 cells, the PBLs were restimulated with peptide MLDLQPETT (SEQ ID NO: 62). To do so the procedure for restimulation, supra is repeated.

8) Cloning by Limiting Dilution

On day 21 after incubation of PBLs, peptide MLDLQPETT (SEQ ID NO: 62) and T2 cells, cells and medium out of the 96 wells were harvested. Viable cells were isolated by Ficoll-procedure and washed in complete RPMI with 15% HPS. This bulk culture of viable cells was cloned by Limiting Dilution. Into each well of a new 96-well-U-bottom plate (Costar, Cambridge, USA, cat. nr. 3799) 50 μl complete RPMI medium with 15% HPS was added together with 100 viable cells (=HPV16 bulk anti MLDLQPETT (SEQ ID NO: 62). For other new 96-well-U-bottom plates this was exactly repeated except for the number of cells for wells: subsequent plates contained dilutions of cells at 10, 1, or 0.3 cells per well. To all wells 20,000 pooled and irradiated (3000 rad) PBL of four different donors and 10,000 pooled and irradiated (10,000 rad) EBV-transformed B-cells of three different HLA-A2.1 donors (VU-4/518/JY) were added together with 50 μl of complete RPMI medium with 15% HPS and peptide MLDLQPETT (SEQ ID NO: 62)in a concentration of 40 μg/ml, Leucoagglutinin in a concentration of 2% (Pharmacia, Uppsala, Sweden,), human recombinant IL-2 in a concentration of 120 IU/ml (Eurocetus, Amsterdam, The Netherlands).

9) Expand Clones

Add per well, in a final volume of 100 μl =>

25,000 viable cells 20,000 irradiated PBL-pool (described supra)

10,000 irradiated EBV-pool (described supra)

2 μg peptide MLDLQPETT (SEQ ID NO: 62)

6 IU recombinant IL-2.

On day 49 a cytotoxicity assay was performed with 65 clones and one bulk sample as effector cells and T2 (with or without the peptide MLDLQPETT (SEQ ID No. 62)) as target cells. Background killing is defined as killing of T2 cells incubated with an irrelevant (but HLA-A2.1 binding) peptide: GILGFVFTL (SEQ ID NO: 64). This influenza matrix protein-derived peptide is the epitope for HLA-A2.1 restricted influenza specific CTL and is known in the art. The HPV bulk (C.B.) anti MLDLQPETT effector cells seemed to be specific for killing MLDLQPETT sensitized cells.

Figure 2:
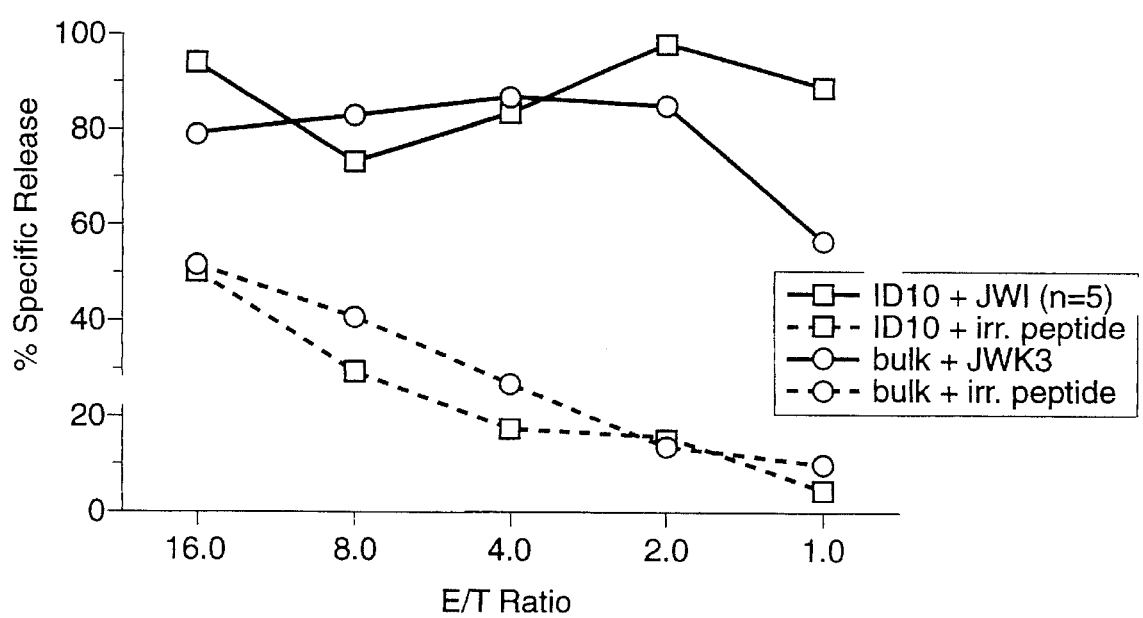
FIG. 2 presents comparative data on the response of HPV clones to various materials, as measured by $^{51}$Cr release assays.

A limiting dilution assay was done with the HPV bulk cells and, after 23 days, a cytotoxicity assay was performed with five clones. Results of a representative clone is shown in FIG. 2.

The data suggest that the peptides of SEQ ID NO: 1–11 are single polypeptides of identified sequences. However, homologs, isoforms or genetic variants of these peptides may exist within or outside the cellular environment. This invention encompasses all such homologs, isoforms or genetic variants of the above peptides provided that they bind to the HLA-A2.1 molecule.

Polypeptides that are homologs of the peptides specifically include those having amino acid sequences which are at least about 40% conserved in relation to the amino acid sequence set forth in Table II, preferentially at least about 60% conserved, and more preferentially at least about 75% conserved.

It will be understood by one of ordinary skill in the art that other variants of the peptides shown above are included within the scope of the present invention. This particularly includes any variants that differ from the above mentioned and synthesized peptides only by conservative amino acid substitution. In particular, replacements of C (cysteine) by A (alanine), S (serine), α-aminobutyric acid and others are included as it is known that cysteine-containing peptides are susceptible to (air) oxidation during synthesis and handling. Many such conservative amino acid substitutions are set forth as sets by Taylor Biol. 188: 233–258 (1986).

Herein the peptides shown above or fragments thereof include any variation in the amino acid sequence, whether by conservative amino acid substitution, deletion, or other processes, provided that the polypeptides bind to the HLA-A2.1 molecule. The fragments of the peptides may be small peptides with sequences of as little as five or more amino acids, said sequences being those disclosed in Table II when said polypeptides bind to the HLA-A2.1 molecule.

Polypeptides larger than the peptides shown are especially included within the scope of the present invention when said polypeptides induce a MAGE-2-specific CTL response in HLA-A2.1 positive individuals and include a (partial) amino acid sequence as set forth in Table II, or conservative substitutions thereof. Such polypeptides may have a length of from 9 to 12, more preferably 9 to 11 or even 9 to 10 amino acids.

This invention includes the use of polypeptides generated by every means, whether genetic engineering, peptide synthesis with solid phase techniques or others. The foregoing peptides may have various chemical modifications made at the terminal ends and still be within the scope the present invention. Also other chemical modifications are possible, particularly cyclic and dimeric configurations. The term "derivatives" intends to cover all such modified peptides.

The polypeptides of the present invention find utility for the prophylaxis, diagnosis and/or treatment or prevention of diseases involving MAGE-2 expressing cells including melanoma cells and other cancer cells.

For all applications the peptides are administered in an immunogenic form. Since the peptides are relatively short, this may necessitate admixture, complexing, combining, conjugation, or chemical binding with an immunogenicity conferring carrier material such as lipids or others or the use of adjuvants.

The magnitude of a prophylactic or a therapeutic dose of polypeptides of this invention will, of course, vary with the group of patients (age, sex, weight, etcetera), the nature of the severity of the condition to be treated, the particular polypeptide of this invention and its route of administration. Any suitable route of administration maybeemployed to achieve an effective dosage of a polypeptide identified by this invention, as well as any dosage form well known in the art of pharmacy. In addition the polypeptides may also be administered by controlled release means and/or delivery devices. They may also be administered incombination with other active substances, such as, in particular, T-cell activating agents like interleukin-2 etc.

The peptides of this invention may also be useful for other purposes, such as diagnostic use. For example, they may be used to check whether a vaccination with a peptide according to the invention has been successful. This may be done in vitro by testing whether said peptide is able to activate T cells of the vaccinated person.

Other aspects of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated peptide selected from the group consisting of SEQ ID NO: 1, SEQ ID NO: 2, SEQ ID NO: 4, SEQ ID NO: 8, SEQ ID NO: 9, and SEQ ID NO: 11.

2. The isolated peptide of claim 1, designated SEQ ID NO: 1.

3. The isolated peptide of claim 1, designated SEQ ID NO: 9.

4. The isolated peptide of claim 1, designated SEQ ID NO: 11.

* * * * *

UNITED STATES PATENT AND TRADEMARK OFFICE
CERTIFICATE OF CORRECTION

PATENT NO. : 5,554,724
DATED : September 10, 1996
INVENTOR(S) : Melief et al.

Page 1 of 1

It is certified that error appears in the above-identified patent and that said Letters Patent is hereby corrected as shown below:

Column 4,
Line 44, after "Williams" insert -- Int. J. -- .
Line 49, change "10.67 M BOP" to -- 0.67 M BOP --.
Line 53, change "Fmocamino" to -- Fmoc amino --.

Column 7,
Line 51, change "p, prides" to -- peptides --.

Column 8,
Line 11, change "46" to -- 48 --.
Line 58, change "post Fico" to -- post Ficoll --.

Column 10,
Line 57, after "Taylor" insert -- J. Mol --.

Signed and Sealed this

Seventh Day of August, 2001

*Attest:*

NICHOLAS P. GODICI
*Attesting Officer*  Acting Director of the United States Patent and Trademark Office